United States Patent [19]

Bolliger

[11] Patent Number: 4,735,944

[45] Date of Patent: Apr. 5, 1988

[54] SPIRO-DIOXOLANES, -DITHIOLANES AND -OXOTHIOLANES, AND THEIR USE IN MENTAL THERAPY

[75] Inventor: Georg Bolliger, Binningen, Switzerland

[73] Assignee: Sandoz Ltd., Basel, Switzerland

[21] Appl. No.: 817,715

[22] Filed: Jan. 10, 1986

[30] Foreign Application Priority Data

| Jan. 16, 1985 [DE] | Fed. Rep. of Germany | 3501225 |
| Feb. 8, 1985 [DE] | Fed. Rep. of Germany | 3504286 |
| Feb. 8, 1985 [DE] | Fed. Rep. of Germany | 3504284 |
| Feb. 8, 1985 [DE] | Fed. Rep. of Germany | 3504281 |

[51] Int. Cl.$^4$ .............. C07D 491/113; A61K 31/395

[52] U.S. Cl. .................... 514/278; 546/19; 548/952; 548/409; 540/466; 540/543; 514/409; 514/210; 514/212; 514/184

[58] Field of Search .............. 546/19; 548/409, 952; 540/466, 543; 514/210, 212, 278, 184, 409

[56] References Cited

PUBLICATIONS

Ridley et al., J. Med. Chem. 1969 12, 931.
Rueppel et al., J. Amer. Chem. Soc. 94, 3877 (1972).
Jones et al., J. Chem. Soc. (B) 1973, 6, 1302.
Jones, II et al., J. Chem. Soc., Perkin Trans II, 1973, 4 337.

*Primary Examiner*—Robert T. Bond
*Attorney, Agent, or Firm*—Gerald D. Sharkin; Robert S. Honor

[57] ABSTRACT

Spiro compounds, comprising a five-membered carbocyclic ring interrupted by two heteroatoms in ring positions 1 and 3 chosen from oxygen and sulfur atoms and in which the carbon atom in ring position 4 is common to a 4 to 8-membered carbocyclic ring interrupted by a nitrogen atom, are useful as pharmaceuticals.

7 Claims, No Drawings

SPIRO-DIOXOLANES, -DITHIOLANES AND -OXOTHIOLANES, AND THEIR USE IN MENTAL THERAPY

The invention relates to the pharmaceutical use of spirodioxolanes, -dithiolanes and -oxothiolanes.

The invention provides a spiro compound, comprising a five-membered carbocyclic ring interrupted by two heteroatoms in ring positions 1 and 3 chosen from oxygen and sulfur atoms and in which the carbon atom in ring position 4 is common to a 4 to 8-membered carbocyclic ring interrupted by a nitrogen atom, in free base or pharmaceutically acceptable acid addition or quaternary ammonium salt form, for use as a pharmaceutical.

These spiro compounds, hereinafter referred to as compounds according to the invention, have the following structure:

$$\underset{1'N}{\overset{(CH_2)_m}{\diagup}} \overset{4}{\diagdown} \underset{(CH_2)_n}{\diagup} \overset{X_1}{\diagdown} \underset{X_2}{\diagup} \Big|_2$$

wherein $X_1$ and $X_2$ independently are oxygen or sulfur and m and n independently are 1, 2, 3 or 4, provided that $m+n \leq 6$.

This basic structure may be substituted by pharmacologically acceptable groups, e.g. in positions 2 and 1'.

The compounds according to the invention possess an asymmetrical carbon atom in position 4 when m and n are different, and depending on the substituents also in further positions, e.g. in position 2. They may therefore appear in racemic or optically active forms. The invention relates to both the racemates and the optically active forms.

The compounds according to the invention may be present in free base form or as pharmaceutically acceptable acid addition or quaternary ammonium salts. The invention relates to the free bases and the acid addition and quaternary ammonium salt forms. Examples of suitable pharmaceutically acceptable acid addition salt forms are the hydrochlorides, hydrogen fumarates and hydrogen maleinates. Examples of pharmaceutically acceptable ammonium salt forms are the iodomethylates.

The invention relates in particular to compounds of formula I $$R_1-N\underset{(CH_2)_n}{\overset{(CH_2)_m}{\diagup}}\diagdown\underset{X_2}{\overset{X_1}{\diagup}}\underset{R_3}{\overset{R_2}{\diagup}} \qquad I$$

wherein $R_1$ is hydrogen, $(C_{1-6})$alkyl optionally substituted by 1 to 6 halogen atoms with an atomic number of 9 to 35, $(C_{3-6})$alkenyl or $(C_{3-6})$alkynyl wherein the multiple bond is not adjacent to the nitrogen atom, $(C_{3-7})$cycloalkyl, $(C_{3-7})$cycloalkyl$(C_{1-2})$alkyl, benzyl, $(C_{2-5})$alkoxycarbonyl, benzoxycarbonyl, $(C_{2-5})$alkanoyl, benzoyl, nicotinoyl, dihydronicotinoyl, N-$(C_{1-4})$alkyl-dihydronicotinoyl, $R_2$ and $R_3$ independently are hydrogen, $(C_{1-6})$alkyl optionally substituted by 1 to 6 halogen atoms with an atomic number of 9 to 35, $(C_{2-6})$alkenyl, $(C_{2-6})$alkynyl, $(C_{3-7})$cycloalkyl or phenyl, or form together a —$(CH_2)_p$— chain wherein p is 2, 3, 4 or 5, $X_1$ and $X_2$ independently are —O— or —S— and m and n independently are 1, 2, 3 or 4, provided that $m+n \leq 6$, and their pharmaceutically acceptable acid addition salts and quaternary ammonium salts, for use as pharmaceuticals.

Any alkyl or alkoxy preferably has one or two carbon atoms and especially one carbon atom. Halogen preferably is fluor or chlor. Preferably m and n are 2 and 2, 3 and 1 or 2 and 1.

The present invention also relates to a process for the production of a spiro compound comprising a five-membered carbocyclic ring interrupted by two heteroatoms in ring positions 1 and 3 chosen from oxygen and sulfur atoms and in which the carbon atom in position 4 is common to a 4 to 8-membered carbocyclic ring interrupted by a nitrogen atom, in free base or pharmaceutically acceptable acid addition or quaternary ammonium salt form, which includes the step of cyclising a corresponding 4 to 8-membered carbocyclic ring interrupted by a nitrogen atom, which bears instead of the five-membered carbocyclic ring a group chosen from hydroxy and mercapto and a group chosen from hydroxymethyl and mercaptomethyl, and recovering the resultant spiro compound or a further spiro compound of claim 10 obtained therefrom in free base or pharmaceutically acceptable acid addition or quaternary ammonium salt form.

The invention in particular relates to a process for the production of a compound of formula I or an acid addition or quaternary ammonium salt thereof, which includes the step of cyclising a compound of formula II $$R_1-N\underset{(CH_2)_n}{\overset{(CH_2)_m}{\diagup}}\diagdown\underset{X_2H}{\overset{X_1H}{\diagup}} \qquad II$$

wherein $R_1$, $X_1$, $X_2$, m and n are as defined above and recovering the resultant compound of formula I or a further compound of formula I obtained therefrom in free base or pharmaceutically acceptable acid addition or quaternary ammonium salt form.

Preferbly the compound of formula II is reacted with a compound of formula III, $$O=C\underset{R_3}{\overset{R_2}{\diagup}} \qquad III$$

wherein $R_2$ and $R_3$ are as defined above.

The reaction is effected under water-splitting conditions and may take place in accordance with known methods, for example using a mild Lewis acid as a catalyst, e.g. boron trifluoride etherate.

A so obtained compound of formula I may be converted into a further compound of formula I using known methods.

Thus a compound of formula I wherein $R_1$ is $(C_{2-5})$alkoxycarbonyl may be reduced in accordance to known methods, for example using lithium-aluminium hydride or aluminium hydride, into a compound of formula I wherein $R_1$ is methyl.

Furthermore a compound of formula I wherein $R_1$ is hydrogen may be converted into a compound of formula I wherein $R_1$ has another significance than hydrogen using a conventional process for the alkylation or acylation on a secondary nitrogen.

Working up of the reaction mixtures obtained according to the above processes, and purification of the compounds of formula I thus obtained, may be effected in accordance with known methods.

The racemates may be separated into the individual optically active components, using known methods, e.g. formation of acid addition salts with optically active acids, and fractionated cristallisation of the diastereoisomeric acid addition salts.

Acid addition salts and quaternary ammonium salts can be produced from the free base forms in known manner, and vice versa.

The starting compounds of formula II are known or may be prepared as follows:

Compounds of formula II wherein $X_1$ and $X_2$ both are —O— may be produced by hydrolysing in accordance with known methods compounds of formula IV

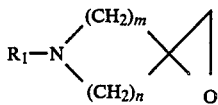

IV wherein $R_1$, m and n are as defined above.

Compounds of formula II wherein $X_1$ is —S— and $X_2$ is —O— may be produced by reacting compounds of formula IV with thioacetic acid and submitting the resulting thioacetates to a basic hydrolysis.

Compounds of formula II wherein $X_1$ and $X_2$ both are —S— may be produced by reacting compounds of formula V

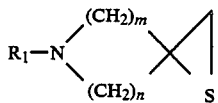

V wherein $R_1$, m and n are as defined above, with thioacetic acid and submitting the resulting thioacetates to a basic hydrolysis.

Compounds of formula II wherein $X_1$ is —O— and $X_2$ is —S— may be produced by reacting compounds of formula V with acetic anhydride and submitting the resulting acetates to a basic or acidic hydrolysis.

The compounds of formula V may be prepared in accordance to known methods from compounds of formula IV, e.g. by reaction with thiourea.

The compounds of formula IV may be produced by reacting compounds of formula VI

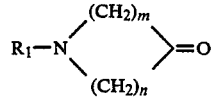

VI wherein $R_1$, m and n are as defined above, with dimethylsulfonium-methylide.

Insofar as the production of the starting products is not described, these are known, or they may be produced by known processes or in analogous manner to known processes.

The compounds of formula I wherein $X_1$ and $X_2$ are both —O— may also be prepared by reacting the compounds of formula IV directly with the compounds of formula III, for example using a mild Lewis acid as a catalyst, e.g. as described in example 2.

Amongst the compounds according to the invention, the 3,7-dimethyl-2,4-dioxo-7-azaspiro[3,4]octane and its iodomethylate, the [2,2-dimethyl-spiro-(1,3-dioxolan-4,3')]-1'-methyl-piperidine-2-one, the spiro-(1,3-dioxolan-4,4')-1'-t.-butyl-piperidine and the [2,2-dimethyl-spiro-(1,3-dioxolan-4,4')]-1'-t.-butyl-piperidine are known from the literature. However no pharmaceutical use of these compounds has been disclosed till now.

It has now surprisingly been found that the compounds according to the invention are useful for the treatment of senile dementia, Alzheimer's disease, Huntington's chorea, tardive dyskinesia, hyperkinesia, mania, acute confusion disorders and glaucoma, as indicated in activity in tests mentioned below.

The compounds according to the invention, exhibit pharmacological activity and are therefore useful as pharmaceuticals, e.g. for therapy.

In particular the compounds show activity in the following tests:

(i) in the observation test in the mouse the compounds at doses from 1 to 300 mg/kg p.o. provoke a prolongation of the wake phase and an increased reactivity to external stimuli, (ii) in the sleep/wake cycle test in chronically implanted rats the compounds at doses from about 1 to about 100 mg/kg p.o. increase the REM sleep phase, and (iii) in the carbon-14 deoxyglucose rat test [according to the principles of L. Sokoloff, Journal of Cerebral Blood Flow and Metabolism 1981, 1, 7–36, H. E. Savaki et al., Brain Research 1982, 233, 347 and J. Mc Culloch et al., Journal of Cerebral Blood Flow and Metabolism 1981, 1, 133–136], the compounds at doses from about 1 to 300 mg/kg p.o. increase the carbon-14 deoxyglucose uptake in particular areas of the brain, particularly the limbic system.

The compounds of the invention are therefore useful for the treatment of senile dementia, Alzheimer's disease, Huntington's chorea, tardive dyskinesia, hyperkinesia, mania, acute confusion disorders and glaucoma.

For these indications, the exact dosage will of course vary depending upon the compound employed, mode of administration and treatment desired. The compounds may be administered by any conventional route, non-oral or preferably orally.

In general, satisfactory results are obtained when administered at a daily dosage of from about 0.05 to 100 mg/kg animal body weight. For the larger mammals, an indicated total daily dosage is in the range from about 1 to about 100 mg of the compound, conveniently administered in divided doses 2 to 4 times a day in unit dosage form containing for example from about 0.3 to about 50 mg of the compound or in sustained release form.

The compound of example 20 a is the preferred compound. The senile dementia and Alzheimer's disease indications are the preferred indications.

Appropriate unit doses for oral administration contain for example about 0.5 to about 15 mg of the compounds, e.g. from 1 to 10 mg. Appropriate doses for parenteral administration contain for example about 0.2 to about 30 mg of the compounds, e.g. from 0.3 to 10 mg.

The compounds may be administered in similar manner to known standards for use in these utilities. The suitable daily dosage for a particular compound will depend on a number of factors such as its relative potency of activity.

It has for example been determined that the preferred compound of the invention, the compound of example 20 a has an $ED_{50}$ between ca. 2.5 and 5 μmol/kg in the $^{14}C$-deoxyglucose test described above. It is therefore indicated that the compound may be administered at daily doses of from 1 to 10 mg p.o.

The compound according to the invention may be administered in free base form or as a pharmaceutically acceptable acid addition or quaternary ammonium salt. Such salts may be prepared in conventional manner and exhibit the same order of activity as the free forms.

The present invention also provides a pharmaceutical composition comprising a compound according to the invention in free base form or in pharmaceutically acceptable acid addition or quaternary ammonium salt form in association with a pharmaceutical carrier or diluent.

The pharmaceutical composition according to the invention may additionally comprise a peripheral cholinergic blocker. Such blockers are known and include e.g. methylscopolamine, methylatropine, tropenzilium and pirenzepine.

The pharmaceutical compositions may be formulated in conventional manner and contain a compound according to the invention alone or in admixture with a pharmaceutical carrier or diluent. Oral pharmaceutical compositions may be in the form of, for example, tablets, dispersible powders, granulates, capsules, sirups, suspensions, solutions or elixiers. Liquid forms may contain for example from about 0.1 to about 5 mg/ml, e.g. 0.5 to 2 mg/ml of a compound. Parenteral pharmaceutical forms may be for example solutions or suspensions, e.g. sterile injectable aqueous solutions.

Oral pharmaceutical compositions may contain excipients such as sweetening agents, aromas, dyes, and conserving agents to provide an elegant and palatable preparation. Tablets may contain conventional pharmaceutical excipients e.g. inertdiluents, dispersing agents, binding agents and lubricating agents.

Suspensions, sirups and elixirs may contain the conventional excipients, e.g. suspending agents and conserving agents. Capsules may contain the compound mixed for example with a solid diluent and a lubricating agent.

For the treatment of glaucoma an especially convenient mode of administration is in the form of an ophthalmic composition comprising the compound according to the invention in free base form or in pharmaceutically acceptable acid addition or quaternary ammonium salt form, in association with an ophthalmic carrier.

The ophthalmic compositions may be administered to the eye in conventional manner and the amount administered may be for example about 0.1 ml.

The compositions may be made in conventional manner for analogous ophthalmic compositions, e.g. in the form of ointments, emulsions or preferably in the form of solutions.

Preferably the composition is isotonic with lacrimal fluids. Antimicrobial agents may be present.

Stable and well tolerated ophthalmic compositions may be made containing for example 0.0025 mg/ml of the compound, preferably at a pH of 4.0 to 7.0.

The pH may be adjusted by appropriate amounts of e.g. sodium hydroxide or buffered with phosphate buffer substances.

The ophthalmic compositions contain suitably about 0.001 to 0.1 mg/ml of the active ingredient.

The pharmaceutical compositions may contain up to 90% by weight of the compound as active agent. Preferred compositions are solid dosage forms, e.g. tablets or capsules.

The compounds according to the invention except the above mentioned compounds known from the literature are novel. Thus the present invention also provides a compound according to the invention, excepting the 3,7-dimethyl-2,4-dioxo-7-azaspiro[3,4]-octane and its iodomethylate, the [2,2-dimethyl-spiro-(1,3-dioxolan-4,3')]-1'-methyl-piperidine-2-one, the spiro-(1,3-dioxolan-4,4')-1'-t.-butyl-piperidine and the [2,2-dimethyl-spiro-(1,3-dioxolan-4,4')]-1'-t.-butyl-piperidine, particularly a compound of formula I as defined above, provided that $X_1$ and $X_2$ are not both —O— when (a) $R_1$ and $R_2$ are methyl, $R_3$ is hydrogen and m and n are 1, or (b) $R_1$ is t.-butyl, $R_2$ and $R_3$ are both H or both methyl and m and n are 2, in free base or pharmaceutically acceptable acid addition or quaternary ammonium salt form.

The invention provides for example an above defined, novel compound of formula I in free base or pharmaceutically acceptable acid addition salt form.

In the following examples, all temperatures are uncorrected and are in degrees centigrade.

Maleinate can also be referred to as maleate.

EXAMPLE 1:
[2-methyl-spiro-(1,3-dioxolane-4,4,')]-1'-ethoxy-carbonyl-piperidine 8 g of 1-ethoxycarbonyl-4-hydroxy-4-hydroxymethyl-piperidine in 100 ml of toluene are cooled to −10° and mixed with 40 ml of acetaldehyde. Then, at a constant temperature, 20 ml of boron trifluoride etherate are slowly added in drops. Stirring is effected for 2 hours, and working up then takes place as follows:

The brown suspension is rendered basic with 200 ml of 2 N sodium hydroxide solution, and is extracted three times with 300 ml of methylene chloride. The combined organic phases are washed with water, dried over sodium sulphate, filtered and concentrated by evaporation. The brown oily residue is distilled under vacuum. 6.5 g of colourless oil are obtained. B.p.: 124°–127°/0.08 mm Hg.

The 1-ethoxycarbonyl-4-hydroxy-4-hydroxymethyl-piperidine required as the starting material can be produced as follows:

(a) Spiro-(oxirane-2,4')-1'-ethoxycarbonyl-piperidine

Dimethylsulphoxonium methylide is produced according to Corey et al., Organic Synth. 49, 78 (1969) from 17.5 g of sodium hydride, 70 g of trimethylsulphoxonium iodide in 500 ml of dimethyl sulphoxide, in a 1.5 liter sulphonation flask which has protection from moisture, and is equipped with a mechanical stirrer, a reflux condenser and a gas feed pipe. After the reaction is complete, the gas feed pipe is replaced by a dropping funnel with a pressure equalizer, the funnel containing 50 g of N-carbethoxy-4-piperidone in 150 ml of dry dimethyl sulphoxide. This solution is added in drops during 15 minutes to the prepared dimethylsulphoxonium methylide. Stirring continues for 1 hour, and the yellow solution is then worked up as follows:

The yellow solution is poured onto 1.2 liters of ice whilst stirring well, and is extracted with 1.5 liters of ether. After re-extraction twice, each time with 1.5 liters of ether, and washing with 600 ml of brine/water (1:1), the ether phases are combined, dried over sodium sulphate, filtered and concentrated by evaporation. The remaining yellow oil is distilled under vacuum. 32 g of colourless, motile oil are obtained. B.p.: 90°–92°/0.1 mm Hg.

(b) 1-ethoxycarbonyl-4-hydroxy-4-hydroxymethyl-piperidine 8.3 g of spiro-(oxirane-2,4')-1'-ethoxycarbonyl-piperidine are hydrolysed in 200 ml of 0.02 N hydrochloric acid solution by heating for 1 hour at 50°. After cooling, the solution is neutralised with 2 N soda solution, and extracted three times with 500 ml of methylene chloride. The combined organic phases are washed with saturated sodium chloride solution, dried over sodium sulphate, filtered and concentrated by evaporation. 8.1 g of the desired diol are obtained as a pure colourless resin, which is used for the cyclisation reaction without further purification.

EXAMPLE 2:
[2-methyl-spiro-(1,3-dioxolane-4,4')]-1'-ethoxy-carbonyl-piperidine 26 g of spiro-(oxirane-2,4')-1'-ethoxycarbonyl-piperidine [prepared as described in example 1 a)] in 200 ml of toluene are cooled to −10°, and mixed with 80 ml of acetaldehyde. Then, at a constant temperature, 35 ml of boron trifluoride etherate are slowly added in drops. Stirring is effected for 2 hours, and working up then takes place as follows:

The brown suspension is rendered basic with 300 ml of 2 N sodium hydroxide solution, and extracted three times with 500 ml of methylene chloride. The combined organic phases are washed with water, dried over sodium sulphate, filtered and concentrated by evaporation. The brown oily residue is distilled under vacuum. 21 g of colourless oil are obtained. B.p.: 124°–127°/0.08 mm Hg.

The following compounds wherein $X_1$ and $X_2$ are —O— are produced analogously to example 1 or 2 (all racemates, optionally mixtures of cis- and trans-diastereoisomers):

| EXAMPLE | $R_1$ | $R_2$ | $R_3$ | m | n | m.p. |
|---|---|---|---|---|---|---|
| 3 | C$_6$H$_5$—CH$_2$— | —CH$_3$ | H | 2 | 2 | 176–179°[1,5] |
| 4 | H | —CH$_3$ | H | 2 | 2 | 157–160°[1,6] |
| 5 | H$_3$C— | —CH$_3$ | H | 2 | 2 | 161–164°[2,7] |
| 6 | C$_6$H$_5$—CH$_2$— | —CH$_3$ | H | 3 | 1 | 186–188°[1,5] |
| 7 | H | —CH$_3$ | H | 3 | 1 | 144–146°[2,7] |
| 8 | C$_2$H$_5$—O—CO— | —CH$_3$ | H | 3 | 1 | colourless oil[10] |
| 9 | H$_3$C— | —CH$_3$ | H | 3 | 1 | 159–162°[3,6] |
| 10 | C$_2$H$_5$—O—CO— | —C$_2$H$_5$ | H | 2 | 2 | colourless oil[11] |
| 11 | H$_3$C— | —C$_2$H$_5$ | H | 2 | 2 | 110–113°[4,8] |
| 12 | H$_3$C— | —C$_6$H$_5$ | H | 2 | 2 | 165–168°[4,9] |
| 13 | H$_3$C— | —CH$_3$ | —CH$_3$ | 2 | 2 | 141–143°[4,8] |
| 14 | H$_3$C— | —CH$_3$ | H | 2 | 1 | 87–89°[3,6] |
| 15 | H$_3$C— | —C≡CH | H | 2 | 2 | 117–120°[4,8] |
| 16 | H$_3$C— | —C$_6$H$_5$ —C$_6$H$_5$ |  | 2 | 2 | 175–178°[4,8] |
| 17 | H$_3$C— | H | H | 2 | 2 | 119–122°[4,8] |
| 18 | H$_3$C— | —CCl$_3$ | H | 2 | 2 | 151–154°[4,5] |
| 19 | H$_3$C— | —(CH$_2$)$_3$— |  | 2 | 2 | 153–155°[4,5] |

[1]hydrochloride
[2]hydrogen fumarate
[3]hydrogen oxalate
[4]hydrogen maleinate
[5]from methylene chloride/ether
[6]from acetone/ethyl acetate
[7]from acetone/ether
[8]from ethanol/ether
[9]from isopropanol/ether
[10]b.p.: 98–102°/0.05 mm Hg
[11]b.p.: 148–150°/0.3 mm Hg The iodomethylate of the racemic [2-methyl-spiro-(1,3-dioxolan-4,4')]-1'-methyl-piperidine is prepared by adding an excess of methyl iodide to a solution of the free base in acetone and separating by succion after 12 hours the precipitated crystals. M.p.: 226°–228° (after recrystallisation in acetone).

EXAMPLE 20: (+)- and (−)-[2-methyl-spiro-(1,3-dioxolane-4,4')]-1'-methyl-piperidine The racemic [2-methyl-spiro-(1,3-dioxolane-4,4')]-1'-methyl-piperidine (free base) obtained in example 5 is separated into the two enantiomers using (−)-di-0,0'-p-toluyl-L-tartaric acid resp. (+)-di-0,0'-p-toluyl-D-tartaric acid and fractional crystallisation:

| EXAMPLE 20a: (−)-enantiomer | EXAMPLE 20b: (+)-enantiomer |
|---|---|
| b.p.: 92–95°/10 mm Hg | b.p.: 92–95°/10 mm Hg |
| $[\alpha]_D^{20} = -23.7°$ (c = 2,0 in ethanol) | $[\alpha]_D^{20} = +23.6°$ (c = 1,1 in ethanol) |
| hydrogen maleinate from isopropanol/ether: m.p.: 136–138° | hydrogen maleinate from isopropanol/ether: m.p.: 136–138° |
| $[\alpha]_D^{20} = -12.9°$ (c = 0,62 in ethanol) | $[\alpha]_D^{20} = +12.9°$ (c = 1,2 in ethanol) |
| iodomethylate from acetone: m.p.: 234–236° | iodomethylate from acetone: m.p.: 234–236° |
| $[\alpha]_D^{20} = -11.1°$ (c = 0,5 in ethanol) | $[\alpha]_D^{20} = +11.0°$ (c = 0,6 in ethanol) |

EXAMPLE 21: cis- and trans-[2-methyl-spiro-(1,3-dioxolane-4,3,')]-1'-methyl-pyrrolidine The cis/trans-diastereoisomeric mixture of [2-methyl-spiro-(1,3-dioxolane-4,3')]-1'-methyl-pyrrolidine obtained in example 14 is separated by chromatography into the cis-diastereoisomers (racemate) and the trans-diastereoisomers (racemate):

| EX. 21a: cis-diastereoisomers | EX. 21b: trans-diastereoisomers |
|---|---|
| hydrogen maleinate from methylene chloride/ether: m.p.: 78–81° | hydrogen maleinate from methylene chloride/ether: m.p.: 94–97° |

EXAMPLE 22: [2-methyl-spiro-(3-oxo-1-thiolane-4,4')]-1'-ethoxycarbonyl-piperidine (a) 1-ethoxycarbonyl-4-hydroxy-4-mercaptomethyl-piperidine 10 g of spiro-(oxirane-2,4')-1-ethoxycarbonyl-piperidine [prepared as described in example 1 (a)] are added in drops under a nitrogen atmosphere to 40 ml of thioacetic acid which has been cooled to 0°. After stirring for 3 hours at 0°, the mixture is rendered basic with 2N soda solution and is extracted three times with 400 ml of methylene chloride. The organic phases are combined, dried over sodium sulphate, filtered and concentrated by evaporation. The clear yellow oil (15.3 g) is taken up in 100 ml of methanol without further purification, and mixed with 10 g of solid potash. After stirring for 6 hours at room temperature under a nitrogen atmosphere, the suspension is filtered over Hyflo, and the filtrate is partitioned between 200 ml of brine/water (1:1) and 600 ml of methylene chloride. After re-extraction twice, each time with 500 ml of methylene chloride, the organic phases are combined, dried over sodium sulphate and concentrated by evaporation. 12.4 g of the title compound are obtained as a yellow resin, which is used for cyclisation without further purification.

(b) [2-methyl-spiro-(3-oxo-1-thiolane-4,4')]-1'-ethoxycarbonyl-piperidine

The yellow resin obtained under a is taken up in 100 ml of toluene, cooled to −10°, and mixed with 40 ml of acetaldehyde. Then, at a constant temperature, 15 ml of boron trifluoride etherate are slowly added in drops. Stirring is effected for 2 hours, and working up then takes place as follows:

The red-brown suspension is rendered basic with 150 ml of 2 N sodium hydroxide solution, and extracted three times with 300 ml of methylene chloride. The combined organic phases are washed with water, dried over sodium sulphate, filtered and concentrated by evaporation. The red-brown oily residue is distilled under vacuum. 4 g of yellowish oil are obtained. B.p.: 137°–143°/0.1 mm Hg.

EXAMPLE 23: [2-methyl-spiro-(3-oxo-1-thiolane-4,4')]-1'-methyl-piperidine

This compound is produced analogously to example 22. Hydrochloride from methylene chloride/ether: M.p.: 138°–140°.

EXAMPLE 24: cis- and trans-[2-methyl-spiro-(3-oxo-1-thiolane-4,3,')]-1'-methyl-pyrrolidine The isomeric mixture is produced analogously to example 22 and is separated by chromatography into the cis-diastereoisomers (racemate) and the trans-diastereoisomers (racemate):

| EX. 24a: cis-diastereoisomers | EX. 24b: trans-diastereoisomers |
|---|---|
| hydrogen maleinate from methylene chloride/ether: m.p.: 106–109° | hydrogen maleinate from methylene chloride/ether: m.p.: 60–65° (decomp.) |

EXAMPLE 25: [2-methyl-spiro-(1,3-dithiolane-4,4')]-1'-ethoxycarbonyl-piperidine (a) spiro-(thiirane-2,4')-1'-ethoxycarbonyl-piperidine 18.5 g of spiro-(oxirane-2,4')-1'-ethoxycarbonylpiperidine [prepared as described in example 1(a)] are added in drops over the course of 15 minutes at −5° to a suspension of 7.6 g of thiourea in 38.2 ml of 15% sulphuric acid. Stirring continues for 2 hours, and the resultant homogeneous, orange solution is then worked up as follows:

The orange solution is heated to room temperature, mixed with 100 ml of 2N soda solution, extracted four times with 400 ml of ether, and the ether phases are washed with 100 ml of brine. The organic phases are combined, dried over sodium sulphate, filtered and concentrated by evaporation. The light yellow clear residue is distilled under vacuum. 15.6 g of the title compound are obtained. B.p.: 91°–93°/0.03 mm Hg.

(b) 1-ethoxycarbonyl-4-mercapto-4-mercaptomethyl-piperidine 10 g of spiro-(thiirane-2,4')-1'ethoxycarbonyl-piperidine are added in drops under a nitrogen atmosphere to a solution, cooled to 0°, of 42 ml of thioacetic acid and 6 g of p-dimethylaminopyridine. After stirring for 2 hours at 0°, the mixture is rendered basic with 2N soda solution, and extracted three times with 400 ml of methylene chloride. The organic phases are subsequently washed in succession with 100 ml each of water, 2N hydrochloric acid solution and water again, then combined, dried over sodium sulphate, filtered and concentrated by evaporation. 16.1 g of a clear yellow oil are obtained, which is taken up in 100 ml of methanol without further purification, and mixed with 9.3 g of solid potash. After stirring for 3 hours under a nitrogen atmosphere, the suspension is filtered over Hyflo, and the filtrate is partitioned between 200 ml of brine/water (1:1) and 600 ml of methylene chloride. After re-extraction twice, each time with 500 ml of methylene chloride, the organic phases are combined, dried over sodium sulphate, and concentrated by evaporation. 14.0 g of the title compound are obtained as a yellow resin, which is used for cyclisation without further purification.

(c) [2-methyl-spiro-(1,3-dithiolane-4,4')]-1'-ethoxycarbonyl-piridine

The resin obtained under b is taken up in 120 ml of toluene, cooled to −10° and mixed with 36 ml of acetaldehyde. Then, at a constant temperature, 15 ml of boron trifluoride etherate are slowly added in drops. Stirring continues for 2 hours, and working up then takes place as follows:

The red-brown suspension is rendered basic with 150 ml of 2N sodium hydroxide solution, and extracted three times with 300 ml of methylene chloride. The combined organic phases are washed with water, dried over sodium sulphate, filtered and concentrated by evaporation. The red-brown oily residue is distilled under vacuum. 4.3 g of yellowish oil are obtained. B.p.: 132°–138°/0.02 mm Hg.

EXAMPLE 26:
[2-methyl-spiro-(1,3-dithiolane-4,4')]-1'-methyl-piperidine

This compound is produced analogously to example 25. Hydrogen maleinate from ethanol/ether: M.p.: 137°–140°.

EXAMPLE 27:
[2-methyl-spiro-(1,3-dithiolane-4,3')]-1'-methyl-pyrrolidine

The cis/trans diastereoisomeric mixture is produced analogously to example 25. Hydrogen maleinate from methanol/ether: M.p.: 115°–119°.

EXAMPLE 28:
[2-methyl-spiro-(3-oxo-1-thiolane-5,4']-1'-ethoxycarbonyl-piperidine (a) 1-ethoxycarbonyl-4-hydroxymethyl-4-mercapto-piperidine 10 g of spiro-(thiirane-2,4')-1'-ethoxycarbonyl-piperidine [prepared as described in example 25 (a)] are dissolved in 5 ml of acetic anhydride and 0.4 ml of pyridine, and heated for 24 hours to 100°. After cooling to room temperature, the mixture is rendered basic with 2N soda solution and extracted three times with methylene chloride. The organic phases are subsequently washed in succession with 50 ml each of water, 2N hydrochloric acid solution and water again, then combined, dried over sodium sulphate, filtered and concentrated by evaporation. 15.8 g of a clear yellow oil are obtained, which is taken up without further purification in 100 ml of methanol which contains 5% HCl gas. After stirring for 16 hours, it is partitioned between 200 ml of brine/water (1:1) and 600 ml of methylene chloride. After re-extraction twice, each time with 500 ml of methylene chloride, the organic phases are combined, dried over sodium sulphate and concentrated by evaporation. 13.7 g of the title compound are obtained as a yellow resin which is used for cyclisation without further purification.

(b) [2-methyl-spiro-(3-oxo-1-thiolane-5,4')]-1'-ethoxycarbonyl-piperidine

The resin obtained under a is taken up in 120 ml of toluene, cooled to −10° and mixed with 40 ml of acetaldehyde. Then, at a constant temperature, 15 ml of boron trifluoride etherate are slowly added in drops. Stirring continues for 2 hours, and working up then takes place as follows:

The red-brown suspension is rendered basic with 150 ml of 2N sodium hydroxide solution, and extracted three times with 300 ml of methylene chloride. The combined organic phases are washed with water, dried over sodium sulphate, filtered and concentrated by evaporation. The red-brown oily residue is distilled under vacuum. 4.1 g of yellowish oil are obtained. B.p.: 128°–135°/0.07 mm Hg.

EXAMPLE 29:
[2-methyl-spiro-(3-oxo-1-thiolane-5,4')]-1'-methyl-piperidine

This compound is produced analogously to example 28. Hydrogen maleinate from ethanol/ether: M.p.: 139°–142°.

EXAMPLE 30: cis- and trans-[2-methyl-spiro-(3-oxo-1-thiolane-5,3')]-1'-methyl-pyrrolidine The isomeric mixture is produced analogously to example 28, and is separated by chromatography into the cis-diastereoisomers (racemate) and the trans-diastereoisomers (racemate):

| EX. 30a: cis-diastereoisomers | EX. 30b: trans-diastereoisomers |
| --- | --- |
| hydrochloride from methylene chloride/ether: m.p.: 136–139° | hydrochloride from methylene chloride/ether: m.p.: 165–168° |

EXAMPLE 31:
[2-methyl-spiro-(1,3-dioxolane-4,4')]-1'-methyl-piperidine 26 ml of sulfuric acid monohydrate are added in drops during 2 hours at 0° under a nitrogen atmosphere to 30 g of lithium aluminium hydride in 1 liter of absolute tetrahydrofurane. Stirring continues for 15 minutes and a solution of 18 g of [2-methyl-spiro-(1,3-dioxolane-4,4')]-1'-ethoxycarbonyl-piperidine (prepared as described in example 2) in 200 ml of absolute tetrahydrofurane is added in drops during 30 minutes at constant temperature.

Working up is effected by diluting with 1 liter ether, addition of 50 ml of a saturated sodium sulphate solution and stirring for 30 minutes. The white suspension is filtered on hyflo, the filter cake washed twice with 500 ml ether and the combined filtrates concentrated by evaporation. 10.2 g of a colourless oil are obtained. M.p. of the hydrogen fumarate: 161°–164° (crystallisation from acetone/ether).

Analogously to example 31, the compounds of examples 9, 11 to 21, 23, 24, 26, 27, 29 and 30 are obtained.

EXAMPLE 32: [2-methyl-spiro (1,3-dioxolane-4,4')]-1'-cyclopropylmethyl-piperidine A suspension of 5 g of [2-methyl-spiro-(1,3-dioxoane-4,4')]-piperidine (compound of example 4), 5.1 g of cyclopropylmethyl chloride, 7.2 g of potassium carbonate and 4.5 g of potassium iodide in 100 ml of absolute dimethylformamide is stirred during 2 hours at 80°. The reaction mixture is concentrated by evaporation and the solid residue is partitioned between water and methylene chloride. The aqueous phase is extracted twice with methylene chloride and the organic extracts washed with few water, dried on sodium sulphate and concentrated to an orange oil. After chromatography on 20 x the quantity of silicagel with methylene chloride/2% methanol as eluent a yellowish oil is obtained. M.p. of the hydrogen maleinate: 147°–150° (crystallisation from ethanol/ether).

Analogously to example 28, the compounds of examples 3, 5, 6, 9, 11 to 21, 23, 24, 26, 27, 29 and 30 are obtained.

What we claim is:

1. A compound of formula I

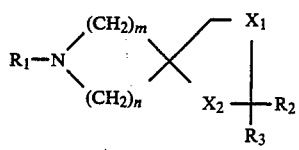

wherein
   $R_1$ is hydrogen, $(C_{1-6})$alkyl optionally substituted by 1 to 6 halogen atoms with an atomic number of 9 to 35, $(C_{3-6})$alkenyl or $(C_{3-6})$alkynyl wherein the multiple bond is not adjacent to the nitrogen atom, $(C_{3-7})$cycloalkyl, $(C_{3-7})$cycloalkyl$(C_{1-2})$-alkyl, benzyl, $(C_{2-5})$alkoxycarbonyl, benzoxycarbonyl, $(C_{2-5})$alkanoyl, benzoyl, nicotinoyl, dihydronicotinoyl, N-$(C_{1-4})$alkyl-dihydronicotinoyl,
   $R_2$ and $R_3$ independently are hydrogen, $(C_{1-6})$alkyl optionally substituted by 1 to 6 halogen atoms with an atomic number of 9 to 35, $(C_{3-6})$alkenyl, $(C_{3-6})$alkynyl, $(C_{3-7})$cycloalkyl or phenyl, or form together a —$(CH_2)_p$— chain wherein p is 2, 3, 4 or 5,
   $X_1$ and $X_2$ independently are —O— or —S— and
   m and n independently are 1, 2, 3 or 4, provided that m+n≦6, provided that $X_1$ and $X_2$ are not both —O— when
   (a) $R_1$ and $R_2$ are methyl, $R_3$ is hydrogen and m and n are 1, or
   (b) $R_1$ is t.-butyl, $R_2$ and $R_3$ are both H or both methyl and m and n are 2,
   in free base or pharmaceutically acceptable acid addition or quaternary ammonium salt form.

2. A compound of claim 1, in free base or acid addition salt form.

3. A compound of claim 1 wherein $R_1$ and $R_2$ are methyl, $R_3$ is hydrogen, $X_1$ and $X_2$ are —O— and m and n are 2, in form of the (—)-isomer.

4. A pharmaceutical composition useful for treating senile dementia, Alzheimer's disease, Huntington's chorea, tardive dyskinesia, hyperkinesia, mania, acute confusion disorder, and glaucoma, comprising a therapeutically effective amount of a compound of claim 1, in association with a pharmaceutical carrier or diluent.

5. A pharmaceutical composition according to claim 4 wherein the compound is (—)-[2-methyl-spiro-(1,3-dioxolane-4,4')]-1'-methyl-piperidine.

6. A method of treating a subject suffering from senile dementia, Alzheimer's disease, Huntington's chorea, tardive dyskinesia, hyperkinesia, mania, acute confusion conditions or glaucoma, which comprises administering a therapeutically effective amount of a compound of claim 1.

7. A method according to claim 6 wherein the compound is (—)-[2-methyl-spiro-(1,3-dioxolane-4,4')]-1'-methyl-piperidine.

* * * * *